US00PP11365P

United States Patent [19]

Leue

[11] Patent Number: Plant 11,365

[45] Date of Patent: Apr. 25, 2000

[54] DOUBLE IMPATIENS PLANT NAMED 'BFP-7812'

[75] Inventor: Ellen F. Leue, DeKalb, Ill.

[73] Assignee: Ball Floraplant, a division of Ball Horticultural Company, West Chicago, Ill.

[21] Appl. No.: 09/113,135

[22] Filed: Jul. 9, 1998

[51] Int. Cl.[7] ..... A01H 5/00

[52] U.S. Cl. ..... Plt./317

[58] Field of Search ..... Plt./317

[56] References Cited

U.S. PATENT DOCUMENTS

P.P. 10,345 4/1998 Cosner et al. ..... Plt./317

*Primary Examiner*—Howard J. Locker
*Assistant Examiner*—Kent L. Bell
*Attorney, Agent, or Firm*—C. A. Whealy

[57] ABSTRACT

A new and distinct cultivar of Double Impatiens plant named 'BFP-7812', characterized by its numerous and consistently double, white-colored flowers; compact, upright and rounded plant habit; good basal branching; and dark green leaves.

1 Drawing Sheet

BACKGROUND OF THE INVENTION

The present invention relates to a new and distinct cultivar of Double Impatiens plant, botanically known as *Impatiens walleriana*, and hereinafter referred to by the cultivar name 'BFP-7812'.

The new Double Impatiens is a product of a planned breeding program conducted by the Inventor in Arroyo Grande, Calif. The objective of the breeding program was to develop new cultivars with excellent basal branching, upright and medium growth habit, numerous large flowers, and interesting flower and foliage colors.

The new Double Impatiens originated from a cross made by the Inventor of the proprietary *Impatiens walleriana* selection 840-4-3 as the male, or pollen parent, with the proprietary *Impatiens walleriana* selection 487-1-1 as the female, or seed parent. The cultivar 'BFP-7812' was discovered and selected by the Inventor as a flowering plant within the progeny of the stated cross in a controlled environment in Arroyo Grande, Calif., on Sep. 15, 1996.

Asexual reproduction of the new cutivar by terminal cuttings taken at Arroyo Grande, Calif., has shown that the unique features of this new Double Impatiens are stable and reproduced true to type in successive generations of asexual reproduction.

SUMMARY OF THE INVENTION

The following traits have been repeatedly observed and are determined to be the unique characteristics of 'BFP-7812'. These characteristics in combination distinguish 'BFP-7812' as a new and distinct cultivar:

1. Numerous and consistently double, white-colored flowers.
2. Compact, upright and rounded plant habit.
3. Good basal branching.
4. Dark green leaves.

The new Double Impatiens can be compared to the cultivar Rosebud™ White, not patented. However, in side-by-side comparisons conducted by the Inventor in Arroyo Grande, Calif., plants of the new Double Impatiens differ from plants of the cultivar Rose™ White in the following characteristics:

1. Plants of the new Double Impatiens are more compact and less vigorous than plants of the cultivar Rosebud™ White.

2. Plants of the new Double Impatiens are more freely branching than plants of the cultivar Rosebud™ White.
3. Plants of the new Double Impatiens are more floriferous than plants of the cultivar Rosebud™ White.
4. Plants of the new Double Impatiens have larger flowers than plants of tyhe cultivar Rosebud™ White.
5. Plants of the new Double Impatiens have stronger peduncles and hold flowers more upright than peduncles of plants of the cultivar Rosebud™ White.

A detailed comparison of plants of the cultivar 'BFP-7812' and the cultivar Rosebud™ White appears in Chart A at the end of the specifications.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of 'BFP-7812'. Flower and foliage colors in the photograph may appear different from the actual colors due to light reflectance.

DETAILED BOTANICAL DESCRIPTION

The cultivar 'BFP-7812' has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Impatiens walleriana* cultivar 'BFP-7812'.

Parentage:

*Male parent.*—Proprietary *Impatiens walleriana* selection 840-4-3.

*Female parent.*—Proprietary *Impatiens walleriana* selection 487-1-1.

Propagation:

*Type cutting.*—Terminal cuttings.

*Time to initiate roots.*—About 7 days at temperatures about 18° C.

*Time to develop roots.*—About 21 days at temperatures about 18° C.

*Rooting habit.*—Fibrous, fine, freely branching.

Plant description:

*Plant form.*—Compact, upright and rounded.

*Growth and branching habit.*—Moderately vigorous. Good basal branching with about six lateral branches at the base, dense and bushy growth. Appropriate for 10 and 12.5-cm containers.

*Plant height.*—About 9.4 cm.

*Crop time.*—About eight weeks are required to produce a finished flowering plant in a 10-cm container from a rooted cutting.

*Lateral branches.*—Length: About 8 cm. Diameter: About 5 mm. Internode length: About 1.4 cm. Color: 145A.

*Foliage description.*—Leaves simple, generally symmetrical, abundant, alternate. Quantity of leaves per lateral branch: About 12. Length: About 3.9 cm. Width: About 2.6 cm. Shape: Ovate with acuminate apex, attenuate base and serrate margin. Texture: Smooth, glabrous. Color: Fully expanded foliage, upper surface: 137B. Fully expanded foliage, lower surface: 138B. Venation, upper surface: 143C. Venation, lower surface: 137D. Petiole: Length: About 1.5 cm. Diameter: About 1.8 mm. Color: 149D.

Flower description:

*Flower type and habit.*—Numerous and consistently double white-colored flowers. Flower buds open similar to a rose in fullness. Freely and continuously flowering. Flowers arise from leaf axils. Usually about 15 flowers and flower buds per lateral branch. Flowers positioned slightly above the foliage and typically face outward and upright. Flowers not persistent.

*Flowering season.*—Year-round under greenhouse conditions. In the garden, flowering is continuous from spring until fall.

*Flower longevity.*—About 7 to 8 days.

*Flower size.*—Diameter: About 3.7 cm. Depth (height): About 2.3 cm.

*Flower buds.*—Length: About 1.4 cm. Diameter: About 1 cm. Shape: Ovoid.

*Color.*—159D.

*Petals.*—Quantity: Numerous, about 25 to 30 per flower. Length: About 1.9 cm. Width: About 1.8 cm. Shape: Rounded to cordate with rounded apex, attenuate to cuneate base and entire margin. Texture: Smooth, slightly iridescent. Color: When opening, upper surface: 155D with slight pink blush. Fully opened, upper surface: 155D. Fully opened, lower surface: 155D. Spur: Length: About 3.1 cm. Color: 145C.

*Peduncles.*—Angle: Upright or outward. Strength: Moderately strong. Length: About 1.7 to 3.5 cm. Color: 145A.

*Reproductive organs.*—None observed.

Disease resistance: Under commercial conditions, resistance to pathogens has not been observed.

Seed development: Seed production has not been observed.

CHART A

| CHARACTERISTIC | 'BFP-7812' | 'ROSEBUD ™ WHITE' |
|---|---|---|
| PLANT HEIGHT | About 9.4 cm | About 11.5 cm |
| BRANCHING HABIT | Freely | Moderate |
| LATERAL BRANCH DIAMETER | About 5 mm | About 3 mm |
| INTERNODE LENGTH | About 1.4 cm | About 1 cm |
| LEAF COLOR, UPPER SURFACE | 137B | 137A |
| LEAF COLOR, LOWER SURFACE | 138B | 147B |
| FLOWER FACING | Upright to outward | Outward to downwards |
| FLOWER DIAMETER | About 3.7 cm | About 3 cm |
| FLOWER DEPTH (HEIGHT) | About 2.3 cm | About 1.7 cm |
| PEDUNCLE ANGLE | Upright to outward | Outward to downwards |
| PEDUNCLE STRENGTH | Moderate | Weak |

It is claimed:

1. A new and distinct cultivar of Double Impatiens plant named 'BFP-7812', as illustrated and described.

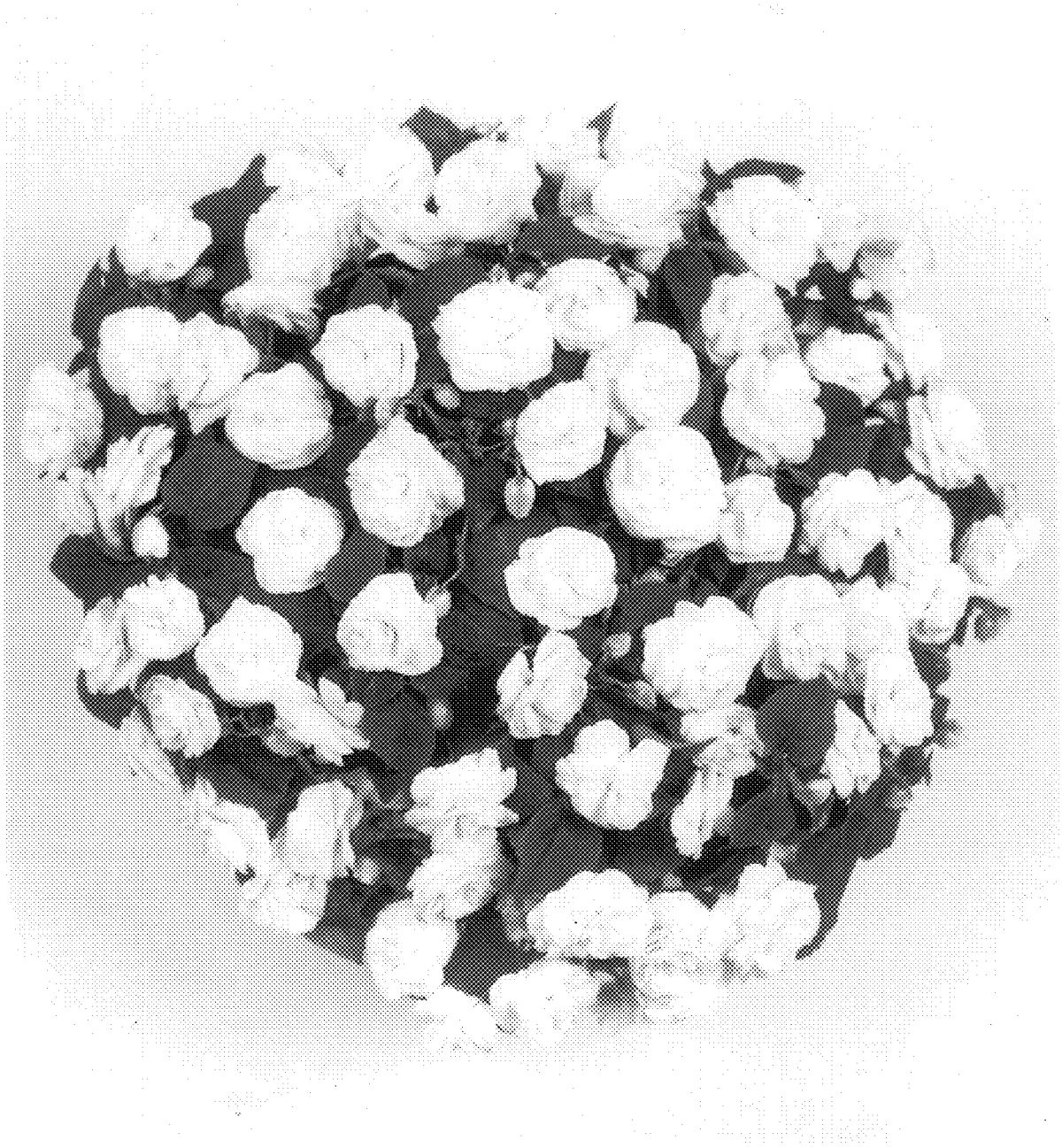

* * * * *